United States Patent
Baker

[11] B 3,987,195
[45] Oct. 19, 1976

[54] CERTAIN BROMOACETOXY ACETYLENES USED AS BACTERICIDES

[75] Inventor: Don R. Baker, Orinda, Calif.

[73] Assignee: Stauffer Chemical Company, Westport, Conn.

[22] Filed: Apr. 4, 1974

[21] Appl. No.: 457,862

[44] Published under the second Trial Voluntary Protest Program on January 27, 1976 as document No. B 457,862.

Related U.S. Application Data

[60] Continuation of Ser. No. 299,990, Oct. 24, 1972, abandoned, which is a division of Ser. No. 853,950, Aug. 28, 1969, Pat. No. 3,711,271.

[52] U.S. Cl. .............................. 424/311; 424/304; 71/67
[51] Int. Cl.² .......................................... A01N 9/24
[58] Field of Search ........................... 424/304, 311

[56] References Cited
UNITED STATES PATENTS
2,931,754  4/1960  Baldridge ........................... 260/487
3,711,271  1/1973  Baker .............................. 424/311 X OTHER PUBLICATIONS
Chemical Abstracts, 61:5509f (1964).

Primary Examiner—Leonard Schenkman
Attorney, Agent, or Firm—Michael J. Bradley

[57] ABSTRACT

Compounds having the formula

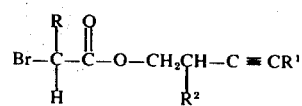

in which R is hydrogen or cyano, and R¹ is hydrogen, alkyl, aryl, nuclear substituted aryl or

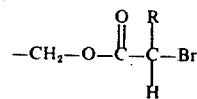

R² is H or methyl, their method of preparation, and the use of these compounds as biocides, such as in controlling fungi, bacteria, and algae.

4 Claims, No Drawings

3,987,195

CERTAIN BROMOACETOXY ACETYLENES USED AS BACTERICIDES

This is a continuation, of application Ser. No. 299,990, filed Oct. 24, 1972, now abandoned which is in turn a division of application Ser. No. 853,950, filed Aug. 28, 1969, now U.S. Pat. No. 3,711,271.

SUMMARY OF THE INVENTION

This invention comprises novel compositions of matter, their method of preparation, and their use as biocides. More particularly, the invention relates to compositions of matter having the formula $$Br-\underset{\underset{H}{|}}{\overset{R}{C}}-\overset{O}{\underset{\|}{C}}-O-CH_2-\underset{\underset{R^2}{|}}{C}H-C\equiv C-R^1$$

wherein R is selected from the group consisting of hydrogen and cyano; $R^1$ is selected from the group consisting of hydrogen; alkyl, preferably having 1 to 8 carbon atoms; aryl, preferably phenyl; nuclear substituted aryl, in which the substituents are lower alkyl, preferably having 1 to 6 carbon atoms, lower alkoxy, preferably having 1 to 6 carbon atoms; chloro, bromo, iodo, nitro or cyano; and $$-CH_2-O-\overset{O}{\underset{\|}{C}}-\underset{\underset{H}{|}}{\overset{R}{C}}-Br$$

in which R is hydrogen or cyano; $R^2$ is hydrogen or methyl, the method of preparation of these compositions, and the use of these compositions as fungicides, bactericides and algaecides.

DESCRIPTION OF PREFERRED EMBODIMENT

In its most preferred form, this invention relates to compositions of matter having the formula $$Br-CH_2-\overset{O}{\underset{\|}{C}}-OCH_2-\underset{\underset{R^2}{|}}{C}-H-C\equiv CR^1$$

wherein $R^2$ is selected from the group consisting of hydrogen and methyl, and $R^1$ is selected from the group consisting of hydrogen, alkyl, especially methyl and ethyl, and $$-CH_2-O\overset{O}{\underset{\|}{C}}-CH_2Br,$$

the method of preparation of these compositions, and the use of these compositions as fungicides, bactericides and algaecides.

The term "nuclear substituted" includes both mono and poly substitution with the specified substituents.

Representative compounds of this invention are as follows:
1-bromoacetoxy-3-butyne
1-bromoacetoxy-3-octyne
1-bromoacetoxy-4-phenyl-3-butyne
1-bromoacetoxy-4-(p-chlorophenyl)-3-butyne
1,5-bis-bromoacetoxy-3-pentyne
1-α-bromocyanoacetoxy-3-pentyne
1-bromoacetoxy-2-methyl-3-butyne While generally it is preferred that the respective R groups be identical in the compounds of the invention having two reacted acyl moieties, it is not a requirement, and compounds wherein the reacted acyl moieties are different are within the contemplation of the invention. The compounds of the present invention are particularly useful in inhibiting the growth of bacteria, fungi and algae.

The compounds of the present invention, except those in which $R^1$ is $$-CH_2-O-\overset{O}{\underset{\|}{C}}-\underset{\underset{H}{|}}{\overset{R}{C}}-Br,$$

may be prepared by reacting a compound of the formula $$Br-\underset{\underset{H}{|}}{\overset{R}{C}}-\overset{O}{\underset{\|}{C}}-hal$$

(reactant A) in which R is hydrogen or cyano and hal is chlorine, bromine, or iodine, with a compound of the formula $HO-CH_2-CHR^2-C\equiv C-R^1$ (reactant B) in which $R^1$ and $R^2$ are as previously defined, exclusive of the radical $$-CH_2-O-\overset{O}{\underset{\|}{C}}-\underset{\underset{H}{|}}{\overset{R}{C}}-Br.$$

Compounds of the formula $$Br-\underset{\underset{H}{|}}{\overset{R}{C}}-\overset{O}{\underset{\|}{C}}-O-CH_2-CHR^2-C\equiv C-CH_2-O-\overset{O}{\underset{\|}{C}}-\underset{\underset{H}{|}}{\overset{R}{C}}-Br$$

in which R and $R^2$ are as above defined can be prepared by reacting about 2 moles of a compound of the formula $$Br-\underset{\underset{H}{|}}{\overset{R}{C}}-\overset{O}{\underset{\|}{C}}-hal$$

wherein R is as above indicated, and hal is chlorine, bromine, or iodine, with a compound of the formula $$HO-CH_2\underset{\underset{R^2}{|}}{C}HC\equiv C-CH_2-OH.$$

The concentrations of the reactants employed are not particularly critical, although generally a slight excess of the acetyl halide (reactant A) will be employed. A suitable concentration will be from about 1.0 mols to about 2.5 mols of monohydroxy compound (reactant B), although additional quantities may be present. Where the hydroxy compound (reactant B) is a diol, the acetyl halide should be present on a basis of from about 2.0 mols to about 3.5 mols per mol of diol. A preferred range for monohydroxy compound reactants (reactant B) would be from about 1.0 to about 2.5 mols of reactant A per mol of reactant B. Similarly, for "diol" compounds (reactant B), a preferred range of concentrations of reactant A should be from about 2.0 to about 3.5 mols, or greater, per mol of reactant (B).

The reactions are preferably carried out under anhydrous conditions in the presence of a base such as pyridine or triethylamine and in a solvent for the reactants. Suitable solvents include ether, benzene, chloroform or tetrahydrofuran. Reactions of this type are normally exothermic so that the addition of heat is not required. In actuality, cooling may sometimes be required to control the reaction rate. The reaction will normally be carried out at a temperature of from about 0°C. to about 55°C. Pressures may be atmospheric, sub-atmospheric, or greater than atmospheric, as desired.

Preparation of the compounds of this invention is illustrated by the following examples:

EXAMPLE I

Preparation of 1-Bromoacetoxy-3-butyne

Approximately 91.3 grams (1.3 moles) of 3-butyne-1-ol is dissolved in chloroform and cooled to about 5°C. About 134.6 grams (185.5 milliliters) of triethylamine and 262.5 grams (1.3 mole) of bromoacetyl bromide diluted in chloroform to equal the volume of triethylamine are added simultaneously to the 1-ol chloroform solution. The temperature is held between 5°C. and 10°C. during addition. After addition, the reaction mixture is stirred for about 1 hour and allowed to come to room temperature. The mixture is washed several times with water and dried over $MgSO_4$. The mixture is decolorized by stirring for about an hour with activated charcoal, and is then concentrated by evaporation to yield 242.1 grams of liquid. N.M.R. spectra confirms the structure of the liquid.

EXAMPLE II

Preparation of 1,5-Bis-bromoacetoxy-3-pentyne

Simultaneously, 80.8 g. of bromoacetyl bromide (0.4 moles) and 40.4 g. of triethylamine (0.4 moles) are added to a stirred solution of 20.0 g. of 3-pentyne-1,5-diol (0.2 moles) dissolved in 350 ml. of tetrahydrofuran. In order to facilitate the simultaneous addition, the volume of the bromoacetyl bromide is equalized to that of the triethylamine by the addition of chloroform. The reaction temperature is maintained at 5°–10°C. by external cooling. After the addition is complete, stirring is continued for 1 hour and the reaction allowed to come to room temperature. The resulting mixture is filtered and the filtrate is diluted with an equal volume of benzene. The diluted filtrate is washed several times with water and then dried over magnesium sulfate. The dried solution is decolorized somewhat by stirring with activated charcoal. After removing the charcoal by filtration, the solution is concentrated in vacuo.

EXAMPLE III

Preparation of 1,5-Bis(bromoacetoxy)-2-methyl-3-pentyne

The procedure of Example II is repeated, using 22.8 grams of 2-methyl-3-pentyne-1,5-diol instead of the 3-butyne-1-ol.

EXAMPLE IV

Preparation of 1-bromoacetoxy-2-methyl-2-pentyne

The procedure of Example I is repeated, utilizing 122 grams of 2-methyl-3-pentyne-1-ol instead of the 3-butyne-1-ol.

The following is a table of certain selected compounds that may be prepared according to the procedure described hereto.

TABLE I $$Br-\underset{\underset{R}{|}}{\overset{\overset{H}{|}}{C}}-\overset{\overset{O}{\|}}{C}-O-CH_2-CHR-C\equiv C-R^1$$

| R | $R^1$ |
|---|---|
| hydrogen | $-CH_2-O-C(O)-CH_2Br$ |
| hydrogen | hydrogen |
| methyl | methyl |
| hydrogen | phenyl |

In order to demonstrate usefulness, the following tests were conducted using 1-bromoacetoxy-3-butyne as exemplary of the compounds of the invention.

In vitro vial test

This test measures the bactericidal and fungicidal properties of a compound when in contact with a growing bacterium or fungus in an artificial medium. The test is conducted by partially filling a 1-ounce vial with malt broth and a 1-ounce vial with nutrient broth. Next, the test compound is added to the vials at a certain concentration, expressed in parts per million, and mixed with the broth. A water suspension of spores of the desired fungi is added to a vial with malt broth and water suspension of cells of the desired bacteria (one organism per vial) is added to a vial with nutrient broth. The vials are then sealed and incubated for one week; at this time the vials are examined and the results recorded. The table below shows the results when 1-bromoacetoxy-3-butyne is tested by the in vitro vial test.

TABLE II

| Fungi | | Bacteria | |
|---|---|---|---|
| Concentration (p.p.m.) which completely inhibited growth | | | |
| Aspergillus niger | Penicillium italicum | Staphyloccus aureus | Escherichia coli |
| 1 | 5 | 50 | 50 |

ALGAECIDAL SCREENING TEST

Sufficient 1-bromoacetoxy-3-butyne is diluted in acetone to give a 0.5 percent solution which is then diluted into 20 milliliters of warm modified Jack Meyers Agar medium. The dilutions are such as to give concentrations of 1, 5, 10 and 50 $\mu g./ml.$ of the test compound in 20 × 100 mm petri dishes. After the agar solidifies, each petri dish is innoculated with organisms of *Scenedesmus obliquus* and *Chlorella pyrenoidosa*. The samples were then allowed to grow at room temperature under fluorescent lamps using a 14 hour light period each day. After two weeks, the results are recorded as set forth in the table below:

TABLE III

| Conc. | Scenedesmus obliguus | Chlorella pyrenoidosa |
|---|---|---|
| 50 μg | control | control |
| 10 μg | control | control |
| 5 μg | control | control |
| 1 μg | control | control |

As can be seen by the test results, the compositions of the invention may be used in killing bacteria, algae, and fungi. The compositions may be applied directly to the particular undesired biological organism or may be applied to a locus to be protected. In either event, it is of course necessary that the unwanted organism receive an effective dosage or amount, i.e., an amount sufficient to kill or retard growth. The compositions may be applied to or in textiles, leather, paint, soaps, paper, wood, plastic, oil, and any other substances susceptible of growth of undesirable biological organisms.

The compositions are normally employed with a suitable carrier and may be applied as a dust, spray, drench or aerosol. The compositions thus may be applied in combination with solvents, diluents, various surface active agents (for example detergents, soaps or other emulsifying or wetting agents, surface active clays) carrier media, adhesives, spreading agents, humectants and the like. They may also be combined with other biologically active compositions, including other fungicides, bactericides, and algaecides, insecticides, growth stimulators, acaricides, herbicides, molluscicides, etc., as well as with fertilizers, soil modifiers, etc. The compositions of the invention may be used in combination with an inert carrier and a surface active or emulsifying agent, and may also be applied in combination with other biologically active materials, in conjunction with a carrier and a surface active or emulsifying agent. The solid and liquid formulations can be prepared by any of the conventional methods well-known by those skilled in the art. Since the amount of active agent required will vary according to the biological organism treated, precise limits on the amounts employed cannot be given. Determination of the optimum effective concentration for a specific application is readily conducted by routine procedures, as will be apparent to those skilled in the art. As indicated, the amount applied in a given case will be an effective amount, i.e., an amount sufficient to give the type of control desired.

Various changes and modifications may be made without departing from the spirit and the scope of the invention described herein, as will be apparent to those skilled in the art to which it pertains.

I claim:

1. A method of killing bacteria comprising applying thereto a bactericidally effective amount of a compound having the formula

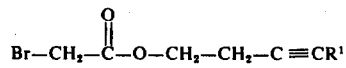

in which $R^1$ is selected from the group consisting of methyl and ethyl.

2. The method of claim 1 in which $R^1$ is methyl.
3. The method of claim 1 in which $R^1$ is ethyl.
4. A method of killing bacteria comprising applying thereto a bactericidally effective amount of a compound having the formula

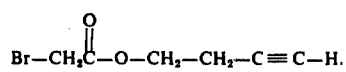

* * * * *